United States Patent [19]

Chang et al.

[11] Patent Number: 4,788,377

[45] Date of Patent: Nov. 29, 1988

[54] PROCESS FOR MANUFACTURING OLEFINS

[75] Inventors: Clarence D. Chang, Princeton; Cynthia T. Chu, Pennington, both of N.J.

[73] Assignee: Mobil Oil Corporation, New York, N.Y.

[21] Appl. No.: 98,713

[22] Filed: Sep. 21, 1987

Related U.S. Application Data

[63] Continuation of Ser. No. 721,145, Apr. 10, 1985, abandoned, which is a continuation of Ser. No. 636,088, Aug. 2, 1984, abandoned, which is a continuation of Ser. No. 487,549, Apr. 22, 1983, abandoned.

[51] Int. Cl.⁴ ............................................. C07C 1/24
[52] U.S. Cl. ............................................. 585/640
[58] Field of Search ........................................ 585/640

[56] References Cited

U.S. PATENT DOCUMENTS

| | | | |
|---|---|---|---|
| 3,271,464 | 9/1966 | Hays et al. | 585/640 |
| 3,894,106 | 7/1975 | Chang et al. | 585/408 |
| 3,894,107 | 7/1975 | Butter et al. | 585/408 |
| 4,025,571 | 5/1977 | Lago | 585/640 |
| 4,025,575 | 5/1977 | Chang et al. | 585/408 |
| 4,052,479 | 10/1977 | Chang et al. | 585/640 |
| 4,062,905 | 12/1977 | Chang et al. | 585/640 |
| 4,066,714 | 1/1978 | Rodewald | 585/640 |
| 4,079,095 | 3/1978 | Givens et al. | 585/640 |
| 4,083,888 | 4/1978 | Caesar et al. | 585/640 |
| 4,083,889 | 4/1978 | Caesar et al. | 585/640 |
| 4,148,835 | 4/1979 | Chen et al. | 585/640 |
| 4,229,608 | 10/1980 | Chen et al. | 585/640 |
| 4,231,899 | 11/1980 | Chen et al. | 502/71 |
| 4,278,565 | 7/1981 | Chen et al. | 585/640 |
| 4,284,529 | 8/1981 | Shihabi | 252/455 Z |
| 4,300,011 | 11/1981 | Rollmann | 585/475 |
| 4,306,106 | 12/1981 | Kerr et al. | 585/640 |
| 4,311,865 | 1/1982 | Chen et al. | 585/408 |
| 4,326,994 | 4/1982 | Haag et al. | 502/85 |
| 4,359,595 | 11/1982 | Rollmann | 585/640 |
| 4,403,044 | 9/1983 | Post et al. | 585/640 |

Primary Examiner—Patrick P. Garvin
Assistant Examiner—George R. Fourson
Attorney, Agent, or Firm—Alexander J. McKillop; Michael G. Gilman; Laurence P. Hobbes

[57] ABSTRACT

Siliceous zeolites, particularly those of the ZSM-5 type having a crystal size of less than one micron have their activity enhanced for the conversion of alcohols and ethers to olefins by steaming.

3 Claims, 3 Drawing Sheets

PROCESS FOR MANUFACTURING OLEFINS

This is a continuation of application Ser. No. 721,145, filed on Apr. 10, 1985, now abandoned, which is continuation of application Ser. No. 636,088, filed on Aug. 2, 1984, now abandoned, which is a continuation of application Ser. No. 487,549, filed on Apr. 22, 1983, now abandoned.

BACKGROUND OF THE INVENTION

1. Field of the Invention

This invention is concerned with the manufacture of light olefin hydrocarbons from lower alcohols and/or their ethers. It is particularly concerned with the catalytic conversion of such alcohols and ethers selectively to mixtures of olefins having up to five carbon atoms. In another aspect, this invention is concerned with a novel catalytic process especially effective for the substantially complete conversion of methanol and/or dimethyl ether to a hydrocarbon mixture characterized by a predominance of olefins.

2. Description of Prior Art

A remarkable growth in the production of synthetic fibers, plastics and rubber has taken place in recent decades. This growth, to a very large extent, has been supported and encouraged by an expanding supply of inexpensive petrochemical raw materials such as ethylene, propylene, and other four and five carbon olefins. Side by side with this remarkable development there has been an increasing demand for alkylate, made by reacting olefins with isobutane, for use as a high octane gasoline component. Environmental factors which limit the lead content of gasoline are likely to aggravate the need for alkylate and for other high-octane gasoline blending stocks.

Burgeoning demand for olefins, particularly ethylene, propylene and butenes, has of course led to periods of shortage, either due to short supply of suitable feedstocks, or to limited processing capacity. In any case, it would appear desirable to provide efficient means for converting raw materials other than petroleum to olefins and/or to high octane gasoline. The dehydration of alcohols, particularly ethanol to ethylene, by catalytic contact with the hydrogen exchanged form of mordenite is disclosed in U.S. Pat. No. 3,244,766, issued Apr. 5, 1966.

The production of olefins from methanol and dimethyl ether by limited conversion with HZSM-5 zeolite catalyst is described in U.S. patent application Ser. No. 537,043, filed Dec. 27, 1974 and now abandoned.

The use of a hydrocarbon diluent to dissipate exothermic heat in a two-stage conversion of methanol to gasoline is described in U. S. Pat. No. 3,931,349.

A two-stage conversion of methanol to olefins and to gasoline which employs a tubular reactor for the second stage is described in U.S. patent application Ser. No. 496,434, filed Aug. 9, 1974, and now abandoned.

U.S. Pat. No. 4,025,576 discloses a process for converting lower monohydric alcohols and their simple or mixed ethers to light olefins by contact with a zeolite catalyst.

U.S. Pat. No. 4,083,889 discloses the production of ethylene from methanol utilizing a zeolite catalyst.

U.S. Pat. No. 4,016,218 discloses the alkylation of aromatic hydrocarbons by contacting them with an olefin alkylating agent in the presence of a catalyst which can be a crystalline zeolite which has been modified by prior thermal treatment from an alpha in the range of 500 to 10,000 to an alpha of less than about 200 but greater than 10.

The processes directed to converting lower alcohols and ethers to olefins ordinarily utilize a fixed bed of catalyst. The feedstock containing methanol and dimethyl ether is introduced at one end of the zone and flowed through the zone whereas the conversion to light hydrocarbons is effected. An effluent stream containing the desired light olefins is removed from the bed.

We have now discovered that, in the catalytic conversion of alcohols to hydrocarbon compounds, particularly in the preparation of olefinic hydrocarbons, the activity of certain zeolite catalysts for olefin production can be desirably and dramatically increased by contacting the vaporized alcohol with certain zeolite catalysts which have been steamed from a higher alpha value to a lower alpha value and which has a crystal size less than one micron. The conversion of alcohols to olefins over the steam-treated small crystal zeolite when compared to conversion over an unsteamed zeolite is considerably enhanced even though the two zeolites compared have equivalent alpha values. For reasons that are not fully understood, it has been found that the crystal size of the zeolite is an important parameter which determines whether or not the activity of said zeolite for olefin production will be enhanced by steaming as will be demonstrated in the examples, zeolites, having a crystal size of one micron or greater do not show a "boost" or enhancement in activity for olefin production when steamed.

BRIEF SUMMARY OF THE INVENTION

In a preferred embodiment of the present invention, a feed comprising one or more compounds, selected from the lower monohydric alcohols with up to four carbon atoms and their simple or mixed ether derivatives, is substantially completely converted to a mixture comprising a major fraction of light olefins, by contacting the feed under suitable reaction conditions with a particular type of crystalline zeolite catalyst, characterized by having a crystal size of less than one micron and preferably from 0.02 to .5 microns and which has been treated by steaming to reduce its alpha value to less than 50, preferably less than 35. Generally, the mixture of olefins produced by this invention, even with a single alcohol feed, contains mostly ethylene, propylene, and the butylenes with a small pentenes component.

The alcohols and corresponding ether derivatives thereof may be manufactured from synthesis gas, i.e. a mixture of CO and H2 made from coal or from natural gas, or they may be produced by fermentation, or they may be manufactured from petroleum fractions in excess supply. The olefin hydrocarbons produced may be converted to alkylate or in aromatics and blended with gasoline, or they may be separated and used as petrochemicals. Thus, in one aspect, the present invention provides a novel means for producing hydrocarbon petrochemicals and fuels from raw materials other than petroleum. In another aspect, as will be more fully described, this invention provides novel means for converting methanol and/or dimethyl ether to low durene-content gasoline or gasoline blending stocks.

As noted above, the mixture of olefins produced by this invention contains mostly ethylene, propylene, and the butylenes with a small pentenes component. This appears to be so regardless whether one feeds methanol, dimethyl ether, ethanol or other permissible feeds as defined elsewhere herein. Thus, it is characteristic of this invention to produce a "conjunct mixture" of olefins, i.e., a product composition unrelated to the exact nature of the feed and from which the feed cannot be recognized. Thus, the conversion of this invention clearly differs from classical dehydration wherein the olefin produced bears a simple relation to the alcohol charged.

It is a noteworthy feature of this invention that highly desirable hydrocarbon by-products are formed along with the olefins. In particular, gasoline boiling range constituents comprising $C_5^+$ paraffins, olefins, naphthenes and aromatics are formed in greater or less quantity, depending on the particular reaction conditions chosen, and these include pentanes, pentenes, and higher boiling materials. Substantially all of these products boil at a temperature less than about 415° F., so that a gasoline boiling range by-product may be recovered when producing olefins by the method of this invention. This gasoline by-product tends to be rich in aromatic hydrocarbons and isoparaffins, and thus characterized by high octane number. When recovered the $C_5^+$ to 415° F. fraction may be used directly as gasoline or as a high octane gasoline blending stock.

As is quite obvious, the olefins which are formed in accordance with the novel process of this invention can be used in a number of different ways, including further conversion by processes well known in the art to gasoline or to gasoline plus distillate. Thus, the novel process of this invention can be looked at as a first step in a multi-step process for making products other than olefins, i.e. in the first step olefins are produced in accordance with the teachings of this invention and in the second step the olefins are converted to other products such as gasoline by techniques well known in the art, e.g. U.S. Pat. No. 4,025,576 or to a mixture of gasoline and fuel oil; for example, e.g. U.S. Pat. No. 4,227,992.

DETAILED DESCRIPTION OF THE INVENTION

The production of olefins by the catalytic conversion of lower alcohols utilizing zeolitic catalysts primarily of the ZSM-5 type is well known in the art. It is also known in the art that in general olefin production is enhanced by operating at less severe operating conditions, including catalytic activity whereas our aromatics are favored at conditions of increased severity. In this connection, German Application No. P 29 35 863.2 discloses the conversion of methanol over high silica-to-alumina ratio ZSM-5 type materials which would inherently have lower alpha values.

It is to be understood that this invention does not merely reside in the use of low alpha value zeolites for the conversion of methanol or even for the conversion of methanol to products which are predominantly olefins. Rather this invention resides in an improvement in the conversion of methanol to olefins with a low alpha zeolite wherein it has been found that the activity of the zeolite for olefins can be enhanced by steaming of the same providing the zeolite has a particular crystal size.

The surprising discovery of the present invention is that the activity for olefin production from alcohol feed is greatly enhanced by the use of a zeolite catalyst having a certain crystal size which has been steamed to reduce its alpha activity from a high value to a lower one under conditions to be described. The lower alcohols that may be charged to the process of this invention include methanol, ethanol, propanol and isopropanol and/or their corresponding ether derivatives. The feed may consist of a relatively pure single alcohol, or mixtures of these alcohols with other components such as higher alcohols. In general, any mixture comprising: methanol or ethanol, or propanol, or isopropanol, is a suitable feed for the present invention.

The preferred charges to the process of the present invention are ethanol and methanol. Particularly preferred are charges comprising substantial fractions, i.e. more than 25 weight percent, of methanol. Mixtures of methanol and dimethyl ether are included as preferred charges.

In the process of the present invention the alcohol and/or ether reactant is contacted with the steamed zeolite catalyst of this invention to produce a product rich in olefinic hydrocarbons.

As has been stated, it is preferred for the purpose of this invention to utilize crystalline zeolites which have had their higher alpha values reduced to less than 50 and preferably to less than 35 by steaming.

The degree of zeolite catalyst activity for all acid catalyzed reaction can be measured and compared by means of "alpha value". The alpha value reflects the relative activity of the catalyst with respect to a high activity silica-alumina cracking catalyst. To determine the alpha value as such term is used herein, n-hexane conversion is determined at a suitable temperature between about 550° F. to 1000° F., preferably at 1000° F. Conversion is varied by variation in space velocity such that a conversion level of up to about 60 percent of n-hexane is obtained to convert to a rate constant per unit volume of zeolite and compared with that of silica-alumina catalyst which is normalized to a reference activity of 1000° F. Catalyst activity of the catalysts are expressed as multiple of this standard, i.e. the silica-alumina standard. The silica-alumina reference catalyst contains about 10 percent $Al_2O_3$ and the remainder $SiO_2$. This method of determining alpha, modified as described above, is more fully described in the Journal of Catalysis, Vol. VI, pp. 278–287, 1966.

It is important to note here that the alpha values thus determined are not a direct measurement of the activity of the zeolite as an agent to catalyze the conversion of alcohols and ethers to olefinic hydrocarbons and, in fact, one of the surprising discoveries of this invention is that the materials which have the same alpha value behave differently and another surprising discovery is that steaming enhances the activity of certain zeolites that have a crystal size of less than one micron whereas steaming does just the opposite to zeolites that have a crystal size greater than one micron. Thus, although it is true that the zeolite must be steam treated to reduce its alpha value to a lower value, the simple fact remains that the zeolite must be of the proper crystal size in order to achieve a catalyst of enhanced activity.

The techniques of steaming zeolites to obtain desired alpha values are known to those skilled in the art.

When the treating atmosphere is steam, temperatures may be used extending from about 500° F. to about 1800° F. depending on the steam pressure, with the use of higher pressure requiring a lower temperature. This treatment is carried on for a period of time sufficient to effect the desired reduction in alpha. Generally, such period will be between about ½ hour and 100 hours. A steam treating atmosphere may be employed which is 100 percent steam or steam admixed with a gas which is substantially inert with respect to the zeolite. It is contemplated that the treatment will generally be effected at atmospheric pressure, but pressures ranging from sub-atmospheric to several hundred atmospheres may be employed. With the use of elevated pressures, temperatures in the lower region of the above-specified range will usually be applicable in achieving the desired reduction in alpha value of the zeolite under treatment. Thus, it has been found, that at elevated steam pressure, the temperature of treatment can be reduced substantially to achieve the same degree of modification.

The crystalline zeolites utilized herein will generally have an alpha value reduced by steaming to less than 50 and preferably to less than 35.

The crystalline zeolites utilized herein are members of a novel class of zeolitic materials which exhibit unusual properties. Although these zeolites have unusually low alumina contents, i.e., high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with silica to alumina mole ratios of at least 12 are useful, it is preferred in some instances to use zeolites having substantially higher silica/alumina ratios, e.g., 1600 and above. In addition, zeolites as otherwise characterized herein but which are substantially free of aluminum, that is zeolites having silica to alumina mole ratios of up to infinity, are found to be useful and even preferable in some instances. Such "high silica" or "highly siliceous" zeolites are intended to be included within this description. Also included within this definition are substantially pure silica analogs of the useful zeolites described herein, that is to say those zeolites having no measurable amount of aluminum (silica to alumina mole ratio of infinity) but which otherwise embody the characteristics disclosed.

The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does not show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

The "Constraint Index" is calculated as follows:

Constraint Index =

-continued $$\frac{\log_{10} \text{(fraction of hexane remaining)}}{\log_{10} \text{(fraction of 3-methylpentane remaining)}}$$

The Constraint Index approximates the ratio of the cracking rate constants for the two hydrocarbons. Zeolites suitable for the present invention are those having a Constraint Index of 1 to 12. Constraint Index (CI) values for some typical materials are:

|  | C.I. |
| --- | --- |
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by wich it is determined, however, admit of the possibility that a given zeolite can be tested under somewhat different conditions and thereby exhibit different Constraint Indices. Constraint Index seems to vary somewhat with severity of operation (conversion) and the presence of absence of binders. Likewise, other variables such as crystal size of the zeolite, the presence of occluded contaminants, etc., may affect the Constraint Index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therfore within the scope of the defined novel class of highly siliceous zeolites are those zeolites which, when tested under two or more sets of conditions within the above-specified range of temperature and conversion, produce a value of the Constraint Index slightly less than 1, e.g. 0.9, or somewhat greater than 12, e.g., 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The novel class of zeolites defined herein is exemplified by ZSM-5, ZSM-11, ZSM-12, ZSM-23, ZSM-35, ZSM-38, ZSM-48, and other similar materials.

ZSM-5 is described in greater detail in U.S. Pat. Nos. 3,702,886 and Re. 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 is more particularly described in pending U.S. patent application Ser. No. 303,276, filed Sept. 17, 1981, and U.S. Pat. No. 4,375,573; both of which are incorporated herein by reference.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38 and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London 1968.

When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing a particularly desired chemical conversion process, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in many cracking processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

It is to be immediately understood that when the zeolitic materials are incorporated into the matrix the resulting composite can have a particle diameter greater than one micron. What is necessary in carrying out the novel process of this invention is that the zeolite which is incorporated in the matrix have a crystal size of less than one micron and not the resulting catalyst composite which is obtained by incorporating said zeolite in said matrix.

Figure 1:
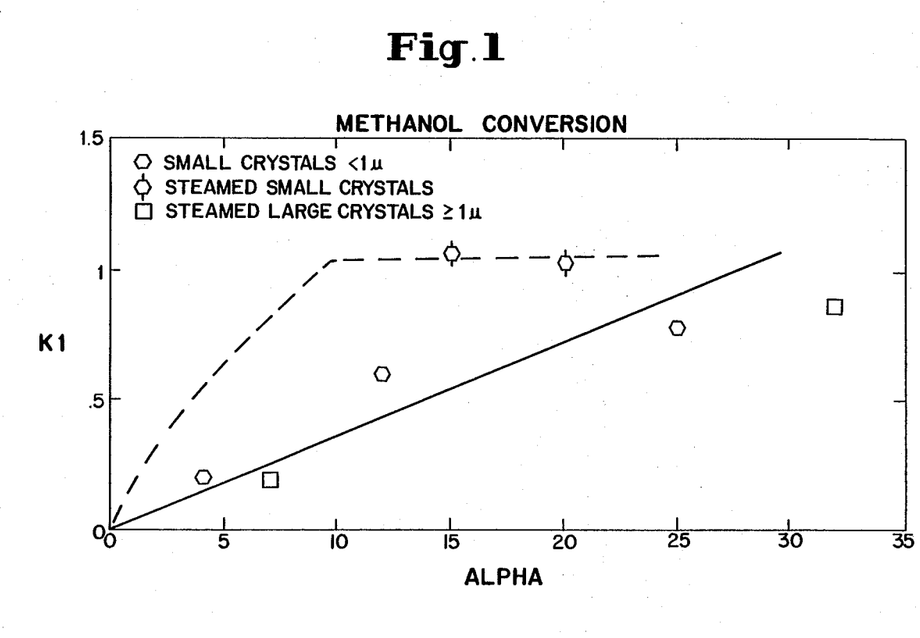
FIG. 1 is a plot of alpha value vs. rate of olefin formation.
Figure 2:
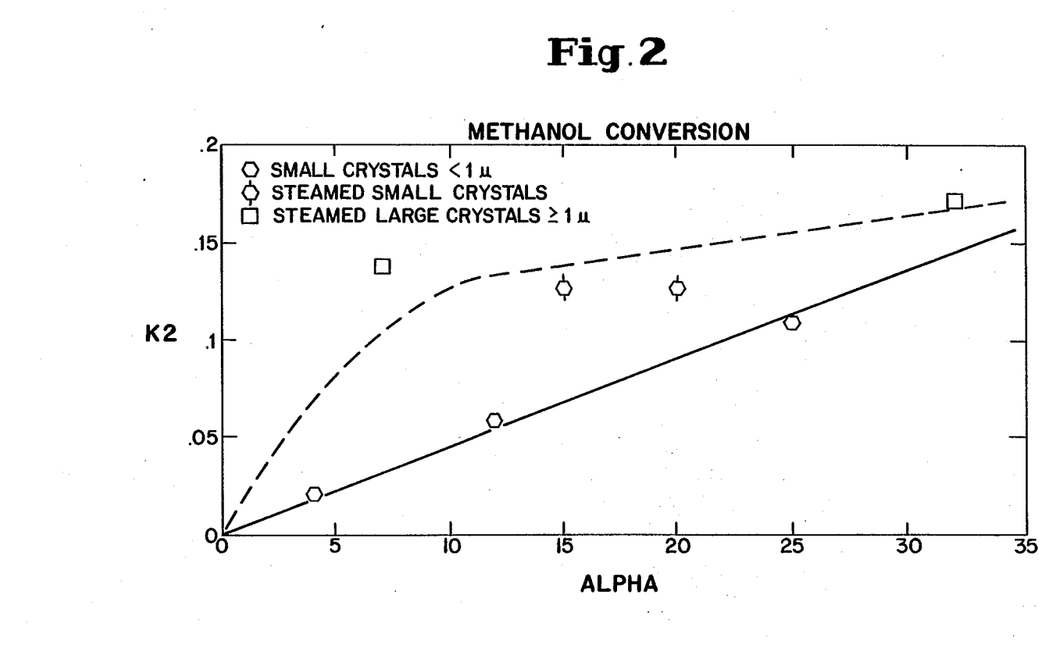
FIG. 2 is a plot of alpha value vs. rate of aromatic formation.
Figure 3:
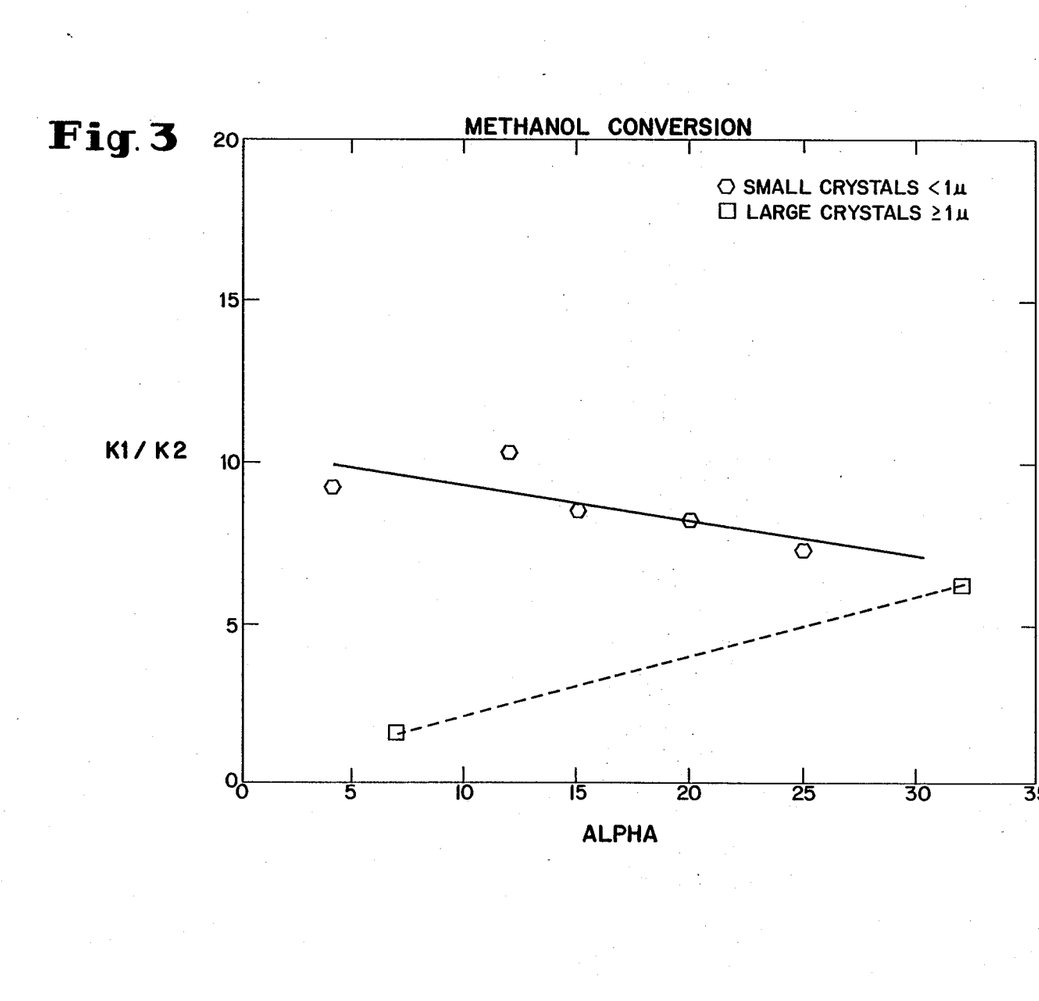
FIG. 3 is a plot of alpha value vs. olefin selectivity.

The above plots were prepared based on the fact that the conversion of methanol could be satisfactorily described by a simple kinetic model:

where A=oxygenates, B=olefins and C=paraffins+aromatics. The rate constants $k_1$ and $k_2$ are associated with olefin formation and aromatics formation, respectively. The ratio $k_1/k_2$ is therefore a measure of olefin selectivity.

The following examples are illustrative of the process of this invention but are not intended to be limited in any aspect.

EXAMPLE 1

Reaction studies were conducted in a ¾" stainless steel microreactor with zeolite catalyst both in the steamed and unsteamed condition. Tests were conducted as atmospheric pressure and LHSV of 1.0 to 300 and the feedstock was pure methanol. The temperature was 500° C. In each case the catalyst was a hydrogen exchanged ZSM-5 zeolite.

In some cases the ZSM-5 was not steamed whereas in other cases the ZSM-5 was steamed at 538° C. for 16 hours to 140 hours at 1 atmosphere of steam.

Both small crystal size (less than one micron) and large crystal size (greater than one micron) ZSM-5 were evaluated and the results are graphically depicted in FIGS. 1, 2 and 3 over a range of alpha values.

The alpha value of the ZSM-5 before steaming ranged from 174–340 alpha for the small crystal size (less than 1 micron) and was 163 alpha for the large crystal (greater than 1 micron).

As can be seen from FIG. 1, steaming enhances the olefin formation rate ($k_1$) of small crystal ZSM-5 only.

FIG. 2 demonstrates that steaming enhances the aromatization rate ($k_2$) of both small and large crystal ZSM-5.

FIG. 3 demonstrates that olefin selectivity ($k_1/k_2$) is enhanced by small crystal ZSM-5.

What is claimed is:

1. In a method for producing a hydrocarbon mixture rich in olefins wherein a feedstock consisting essentially of an alcohol or ether or mixture thereof is contacted with crystalline zeolite having an alpha value the improvement which comprises utilizing a crystalline zeolite ZSM-5 of no greater than 50, in the hydrogen form having a crystal size of about 0.02–0.5 micron which has been steamed from a higher alpha value down to an alpha value between 5 and 35 prior to contact with said feedstock.

2. The method of claim 1 wherein the feedstock is methanol.

3. The method of claim 1 wherein said ZSM-5 is incorporated in a matrix.

* * * * *

UNITED STATES PATENT AND TRADEMARK OFFICE
CERTIFICATE OF CORRECTION

PATENT NO. : 4,788,377
DATED : November 29, 1988
INVENTOR(S) : Clarence D. Chang and Cynthia T-W. Chu It is certified that error appears in the above-identified patent and that said Letters Patent is hereby corrected as shown below:

Col. 5, line 30, delete "conducive", insert -- conductive--.

Col. 7, line 29, delete "wich", insert --which--.

Col. 11, line 28, delete "3/4"", insert --3/8"--.

Col. 12, line 23, after "value", insert --of no greater than 50,--.

Col. 12, line 25, after "ZSM-5", delete "of no greater than 50,"

Signed and Sealed this

Twenty-fourth Day of April, 1990

Attest:

HARRY F. MANBECK, JR.

*Attesting Officer*      *Commissioner of Patents and Trademarks*